United States Patent
Saitoh et al.

(10) Patent No.: US 7,453,567 B2
(45) Date of Patent: Nov. 18, 2008

(54) FLUORESCENCE LIFETIME DISTRIBUTION IMAGE MEASURING SYSTEM AND ITS MEASURING METHOD

(75) Inventors: Haruhisa Saitoh, Hamamatsu (JP); Hirotoshi Terada, Hamamatsu (JP)

(73) Assignee: Hamamatsu Photonics K.K., Shizuoka (JP)

( * ) Notice: Subject to any disclaimer, the term of this patent is extended or adjusted under 35 U.S.C. 154(b) by 443 days.

(21) Appl. No.: 10/516,076

(22) PCT Filed: May 28, 2003

(86) PCT No.: PCT/JP03/06702

§ 371 (c)(1),
(2), (4) Date: Nov. 29, 2004

(87) PCT Pub. No.: WO03/100399

PCT Pub. Date: Dec. 4, 2003

(65) Prior Publication Data

US 2005/0157292 A1     Jul. 21, 2005

(30) Foreign Application Priority Data

May 29, 2002   (JP) ............................. 2002-156276

(51) Int. Cl.
*G01J 3/30* (2006.01)
*G01J 3/28* (2006.01)
(52) U.S. Cl. .................. 356/317; 250/459.1; 250/458.1
(58) Field of Classification Search ................. 356/317, 356/318, 417; 250/458.1
See application file for complete search history.

(56) References Cited

U.S. PATENT DOCUMENTS 5,323,008 A    6/1994   Studholme et al.
5,418,371 A *  5/1995   Aslund et al. ............ 250/458.1

(Continued)

FOREIGN PATENT DOCUMENTS

GB           2 231 958 A     11/1990

(Continued)

OTHER PUBLICATIONS

Wang, X.F. et al., "Fluorescence Lifetime Imaging Microscopy (FLIM): Instrumentation and Applications", Critical Reviews in Analytical Chemistry, 23 (5):369-395 (1992).

(Continued)

*Primary Examiner*—L. G Lauchman
(74) *Attorney, Agent, or Firm*—Drinker Biddle & Reath LLP

(57) ABSTRACT

Pulse excitation light, emitted from a laser light source 10, is scanned in a first direction by a first scanning means 100, scanned in a second direction, perpendicular to the first direction, by a second scanning means 120, converged by an objective optical system 140, and illuminated onto sample 50. Fluorescences, emitted from sample 50, are output from objective optical system 140 to second scanning means 120, scanned in the second direction, perpendicular to the first direction, and output to a light separation means 110 by second scanning means 120, output from light separation means 110 to a streak camera, and recorded as variations of time of the fluorescence intensities by streak camera 30. Fluorescence lifetimes are calculated based on these variations with time of the fluorescence intensities and a fluorescence lifetime distribution image is prepared.

8 Claims, 6 Drawing Sheets

U.S. PATENT DOCUMENTS

| | | | | |
|---|---|---|---|---|
| 6,134,002 | A * | 10/2000 | Stimson et al. | 356/326 |
| 6,321,111 | B1 * | 11/2001 | Perelman et al. | 600/477 |
| 6,496,267 | B1 * | 12/2002 | Takaoka | 356/497 |
| 6,879,394 | B2 * | 4/2005 | Amblard et al. | 356/301 |
| 6,958,858 | B2 * | 10/2005 | Engelhardt et al. | 359/388 |
| 7,002,162 | B1 * | 2/2006 | Fujimoto et al. | 250/458.1 |

FOREIGN PATENT DOCUMENTS

| | | |
|---|---|---|
| GB | 2 323 237 | 9/1998 |
| JP | 59-104519 | 6/1984 |
| JP | 1-227948 | 9/1989 |
| JP | 11-118716 | 4/1999 |
| JP | 2000-088751 | 3/2000 |
| JP | 2001-194305 | 7/2001 |
| JP | 2001-356272 | 12/2001 |
| WO | WO 02/10727 A1 | 2/2002 |

OTHER PUBLICATIONS

Sytsma, J. et al., "Time-Gated Fluorescence Lifetime Imaging and Microvolume Spectroscopy Using Two-Photon Excitation", Journal of Microscopy, 191:39-51 (Jul. 1998).

Ossler, F. et al., "Two-Dimensional Visualization of Fluorescence Lifetimes by Use of a Picosecond Laser and a Streak Camera", Applied Optics, 37 (12):2303-2314 (Apr. 1998).

* cited by examiner

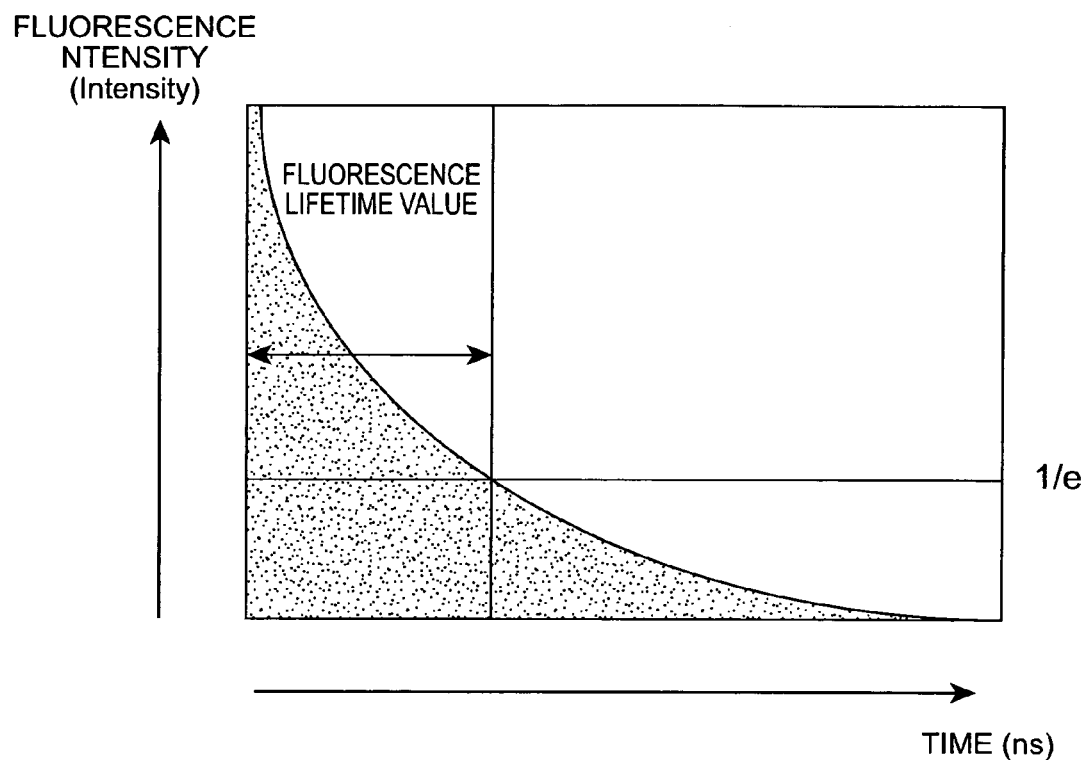

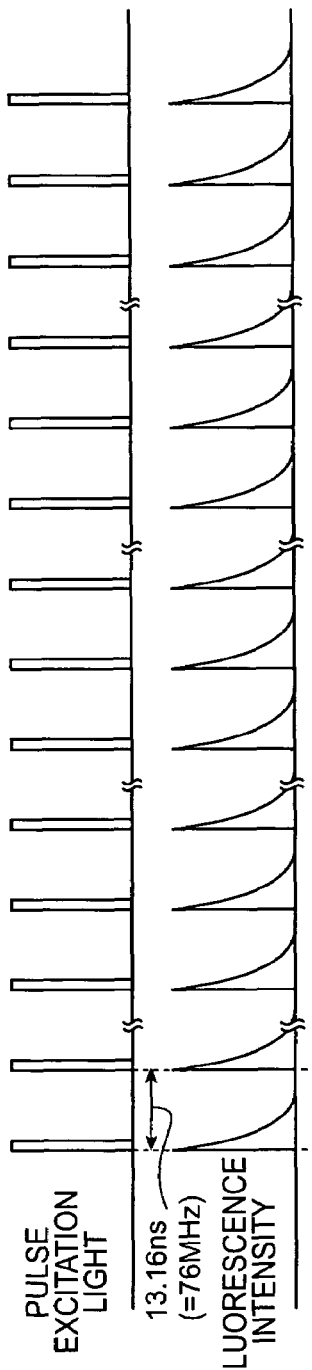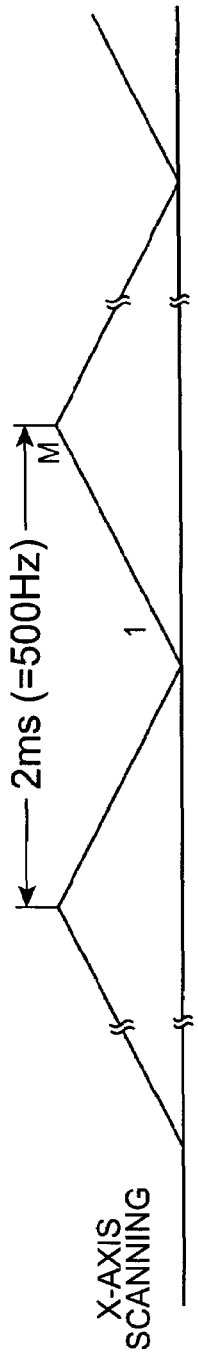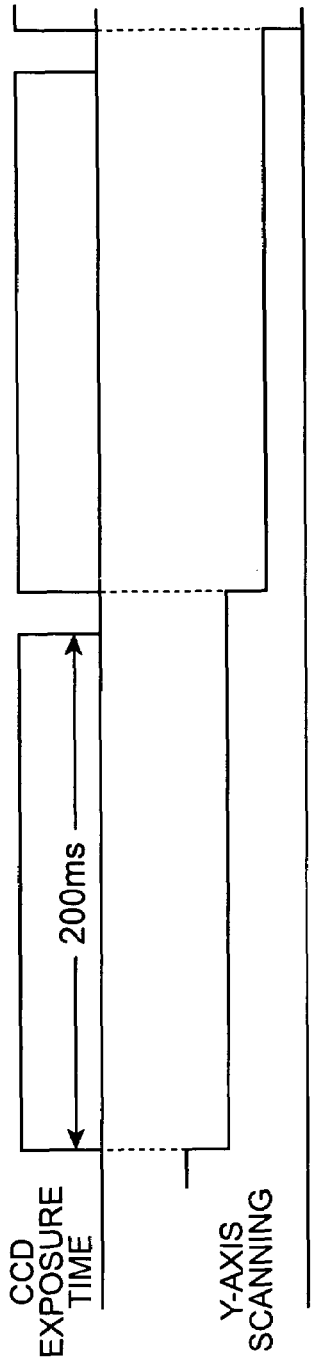

FLUORESCENCE LIFETIME DISTRIBUTION IMAGE MEASURING SYSTEM AND ITS MEASURING METHOD

TECHNICAL FIELD

This invention concerns a fluorescence lifetime distribution image measurement device and measurement method for acquiring a fluorescence lifetime distribution image of the fluorescence emitted from a sample illuminated with an excitation light.

BACKGROUND ART

When an excitation light is illuminated onto a measured object, fluorescence is emitted from fluorescent substances contained in the measured object. The intensity of the fluorescence decays exponentially with the elapse of time from the time of illumination of the excitation light. The fluorescence lifetime expresses the decay characteristic of this fluorescence decay curve and this fluorescence lifetime is determined by the type of fluorescent substance.

In recent years, a measurement method called FLIM (Fluorescence Lifetime Imaging Microscopy), which enables reactions within cells to be measured at high precision by the imaging of the distribution of the fluorescence lifetime values of cells stained by a fluorescent protein or fluorescent dye, has been proposed, and this method is described in the paper, "Fluorescence Lifetime Imaging Microscopy (FLIM): Instrumentation and Applications" (Critical Reviews in Analytical Chemistry, 23(5): 369-395 (1992)). With this measurement method, variations in the fluorescence lifetime, for example, of a fluorescent protein for examining whether or not a particular gene is expressed within a cell, a fluorescent dye that enables measurement of the ionic concentration of calcium, etc., or a fluorescent dye that enables measurement of the pH within a cell, are measured to enable the forming of an image of the distribution of gene expression, ion concentration, pH, etc., within a cell.

As such FLIM measurement methods, a method of combining time-correlation counting by a PMT and laser scanning, a time-resolved image measurement method using a gated image intensifier, and a method using a streak camera are known.

DISCLOSURE OF THE INVENTION

However, the abovementioned prior-art examples had the following problems. That is, with the method using time-correlation counting by a PMT, since only a single photon can be measured for each pulse of excitation light, the measurement time is too long and reactions within a cell, which changes with time, cannot be followed.

With the method using a gated image intensifier, since the fluorescence lifetime is measured by the gated method, the fluorescence acquisition efficiency is poor, and bleaching of the cell or other biological sample and damaging of the sample itself occur due to the effects of the excitation laser.

Meanwhile, with the prior-art method using a streak camera, though the time resolution and sensitivity are high, bleaching of the cell or other biological sample and damaging of the sample itself occur due to the effects of the excitation laser.

This invention has been made to resolve the above issues, and an object thereof is to provide a fluorescence lifetime distribution image measurement device and measurement method, with which the damaging of a cell or other sample can be minimized and measurement within a short time can be realized.

This invention's fluorescence lifetime distribution image measurement device is a fluorescence lifetime distribution image measurement device for measuring the distribution in a sample of the lifetimes of fluorescences emitted from the sample upon illumination of the sample with pulse excitation light and comprises: a laser light source, emitting the pulse excitation light; a measurement optical system, guiding the pulse excitation light emitted by the laser light source to the sample and thereby illuminating the sample and guiding and outputting the fluorescences emitted from the sample; a streak camera, recording the variations with time of the fluorescence intensities of the fluorescences that arrive upon being output from the measurement optical system; and a fluorescence lifetime distribution image creation means, calculating the fluorescence lifetimes based on the variations with time of the fluorescence intensities recorded by the streak camera and creating a fluorescence lifetime distribution image; the measurement optical system in turn comprising a first scanning means, a light separation means, a second scanning means, and an objective optical system, the first scanning means scanning the pulse excitation light, emitted by the laser light source, in a first direction, the light separation means guiding the pulse excitation light, arriving from the first scanning means, to the second scanning means and guiding the fluorescences, arriving from the second scanning means, to the streak camera, and the second scanning means scanning the pulse excitation light, arriving from the light separation means, in a second direction perpendicular to the first direction and guiding the fluorescences, output and arriving from the objective optical system, to the light separation means while scanning the fluorescences in the second direction perpendicular to the first direction. The objective optical system is in a conjugate positional relationship with respect to the first scanning means and the second scanning means, converges the pulse excitation light that has been scanned in the first direction and second direction respectively and thereby illuminates the pulse excitation light onto respective scanning points on the sample and outputs the fluorescences, emitted from the respective scanning points upon illumination of the pulse excitation light, to the second scanning means.

With this invention's fluorescence lifetime distribution image measurement device, the pulse excitation light, emitted from the laser light source, is output to the measurement optical system, the pulse excitation light, output to the measurement optical system, is scanned and output in the first direction by the first scanning means, the pulse excitation light, scanned and output in the first direction, is scanned and output in the second direction perpendicular to the first direction by the second scanning means, and the pulse excitation light, scanned and output in the second direction, is converged by the objective optical system and illuminated onto the sample. The fluorescences, emitted from the sample when the pulse excitation light is illuminated onto the sample, are output by the objective optical system to the second scanning means, and the fluorescences, output to the second scanning means, are scanned in the second direction perpendicular to the first direction by the second scanning means and output to the light separation means. Here, the pulse excitation light and the fluorescences reciprocate through the second scanning means so that on the streak camera, the fluorescences are not scanned in the second scanning direction but are scanned only in the first scanning direction. The fluorescences that have been output to the light separation means are output to the streak camera by the light separation means, and the fluorescences output to the streak camera are recorded as the variations with time of the fluorescence intensities of the fluorescences by the streak camera. Then based on the variations with time of the fluorescence intensities recorded by the streak camera, the fluorescence lifetimes are calculated and the fluorescence lifetime distribution image is prepared.

With this invention's fluorescence lifetime distribution image measurement device, the objective optical system is preferably positioned at a position at which the convergence points are set inside the sample, the pulse width of the pulse excitation light is preferably no more than 150 fs, the peak power density of the pulse excitation light at each convergence point is preferably no less than $1\times10^5$ W/cm$^2$, and the wavelength of the pulse excitation light is preferably no less than $\lambda$ and no more than $2\lambda$ with $\lambda$ being the maximum wavelength of light that can excite the sample and cause fluorescence. Two-photon excitation can thereby be caused by the pulse excitation light at the convergence points.

With this invention's fluorescence lifetime distribution image measurement device, the wavelength of the pulse excitation light is preferably no less than 750 nm and no more than 1000 nm. Two-photon excitation can thereby be caused in a cell or other sample stained by a fluorescent protein or a fluorescent dye.

With this invention's fluorescence lifetime distribution image measurement device, the position of the objective optical system preferably moves along a direction perpendicular to both the first direction and the second direction. Since this enables measurement of the fluorescence lifetimes in the depth direction of the sample as well, a three-dimensional fluorescence lifetime distribution image can be obtained.

With this invention's fluorescence lifetime distribution image measurement device, the first scanning means and the second scanning means are respectively galvanomirrors, and the light separation means is preferably a dichroic mirror.

This invention's fluorescence lifetime distribution image measurement method is a fluorescence lifetime distribution image measurement method for measuring the distribution in a sample of the lifetimes of fluorescences emitted from the sample upon illumination of the sample with pulse excitation light and comprises: a first step of generating the pulse excitation light of a pulse width of no more than 150 fs, a peak power density at each convergence point of no less than $1\times10^5$ W/cm$^2$, and a wavelength of no less than $\lambda$ and no more than $2\lambda$, where $\lambda$ is the maximum wavelength of light that can excite the sample and cause fluorescence; a second step of scanning the pulse excitation light in a first direction; a third step of scanning the pulse excitation light, which has been scanned in the first direction, in a second direction perpendicular to the first direction; a fourth step of converging the pulse excitation light, which has been scanned in the first direction and the second direction, respectively, onto respective scanning points inside the sample; a fifth step of recording the variations with time of the fluorescence intensities of the fluorescences, emitted from the respective scanning points by the illumination of the converged pulse excitation light; and a sixth step of calculating the fluorescence lifetimes based on the recorded variations with time of the fluorescence intensities and creating a fluorescence lifetime distribution image.

With this invention's fluorescence lifetime distribution image measurement method, the pulse excitation light, which is emitted in the first step and has a pulse width of no more than 150 fs, a peak power density at the convergence point of no less than $1\times10^5$ W/cm$^2$, and a wavelength of no less than $\lambda$ and no more than $2\lambda$, where $\lambda$ is the maximum wavelength of light that can excite the sample and cause fluorescence, is scanned in the first direction in the second step. The pulse excitation light, which has been scanned in the first direction, is scanned in the second direction perpendicular to the first direction in the third step. The pulse excitation light, which has been scanned in the first direction and the second direction, respectively, is converged in the interior of the sample in the fourth step, and the variations with time of the fluorescence intensities of the fluorescences, emitted due to illumination of the converged pulse excitation light, are recorded in the fifth step. In the sixth step, the fluorescence lifetimes are calculated based on the recorded variations with time of the fluorescence intensities and a fluorescence lifetime distribution image is prepared.

BRIEF DESCRIPTION OF THE DRAWINGS

FIG. 5 is a diagram showing a fluorescence lifetime profile.

FIG. 6A is a diagram illustrating the timing at which pulse excitation light is emitted.

FIG. 6B is a diagram illustrating the variations with time of the fluorescence intensities that are detected by the streak camera.

FIG. 6C is a diagram illustrating the variation with time of the sweep voltage that is applied to the streak camera.

FIG. 6D is a diagram illustrating the timing of scanning in the X-axis direction.

FIG. 6E is a diagram illustrating the timing by which the CCD picks up images.

FIG. 6F is a diagram illustrating the timing of scanning in the Y-axis direction.

BEST MODE FOR CARRYING OUT THE INVENTION

An embodiment of this invention shall now be described with reference to the attached drawings. In the description using the drawings, the same elements shall be provided with the same symbols and redundant description shall be omitted.

With this invention's fluorescence lifetime distribution image measurement device, a sample is excited by two-photon excitation. Two-photon excitation is a phenomenon that occurs when the intensity of laser light is made extremely strong. Two-photon excitation shall now be described briefly.

If the photon energy hv is less than the absorption bandgap $E_G$ of a sample 50, the sample cannot be excited. The condition for the occurrence of absorption in sample 50 is therefore, hv>$E_G$. However, when the intensity of pulse excitation light is made extremely high, sample 50 is excited by the condition: nhv>$E_G$ (where, n=2, 3, 4, ...). This phenomenon is called multiphoton excitation and in the case of n=2, the phenomenon is called two-photon excitation. In the case of a pulse wave, the intensity of the laser light is determined by the peak power density (W/cm$^2$) at each convergence point of the laser light and, for example, multiphoton absorption occurs at the condition of a peak power density of no less than $1\times10^5$ (W/cm$^2$). The peak power density is determined by: (energy per single pulse of laser light at each convergence point)÷(cross sectional area of the beam spot of laser light×pulse width).

In comparison to single-photon excitation, a laser of long wavelength and low energy can be used with two-photon excitation. As advantages of being able to use a laser of long wavelength, low damage of a cell or other sample and enabling of observation of comparatively deep regions of sample due to the ability of the laser to penetrate deeply into tissue can be cited. Also, it is said that two-photon excitation occurs when two photons arrive substantially simultaneously and occurs substantially in proportion to the square of light intensity, and fluorescent molecules are excited only at each convergence point of the laser light. Fluorescence bleaching at non-observed parts outside each convergence point can thus be prevented, and observation over a long period of time and observation of a wide range of tissue or other sample are enabled. The convergence point refers to the location onto which the laser light converges.

Due to the above reasons, two-photon excitation is essential for measurement of the fluorescent lifetimes of cells and other biological samples. The present inventor thus prepared a prototype of a slit light fluorescence lifetime distribution image measurement device and tested a method of causing two-photon excitation by slit light. However, due to the low excitation efficiency of two-photon excitation, fluorescence lifetime data could not be acquired with slit light. The present inventor thus put effort into further development and thereby completed the invention of the present Application.

Figure 1:
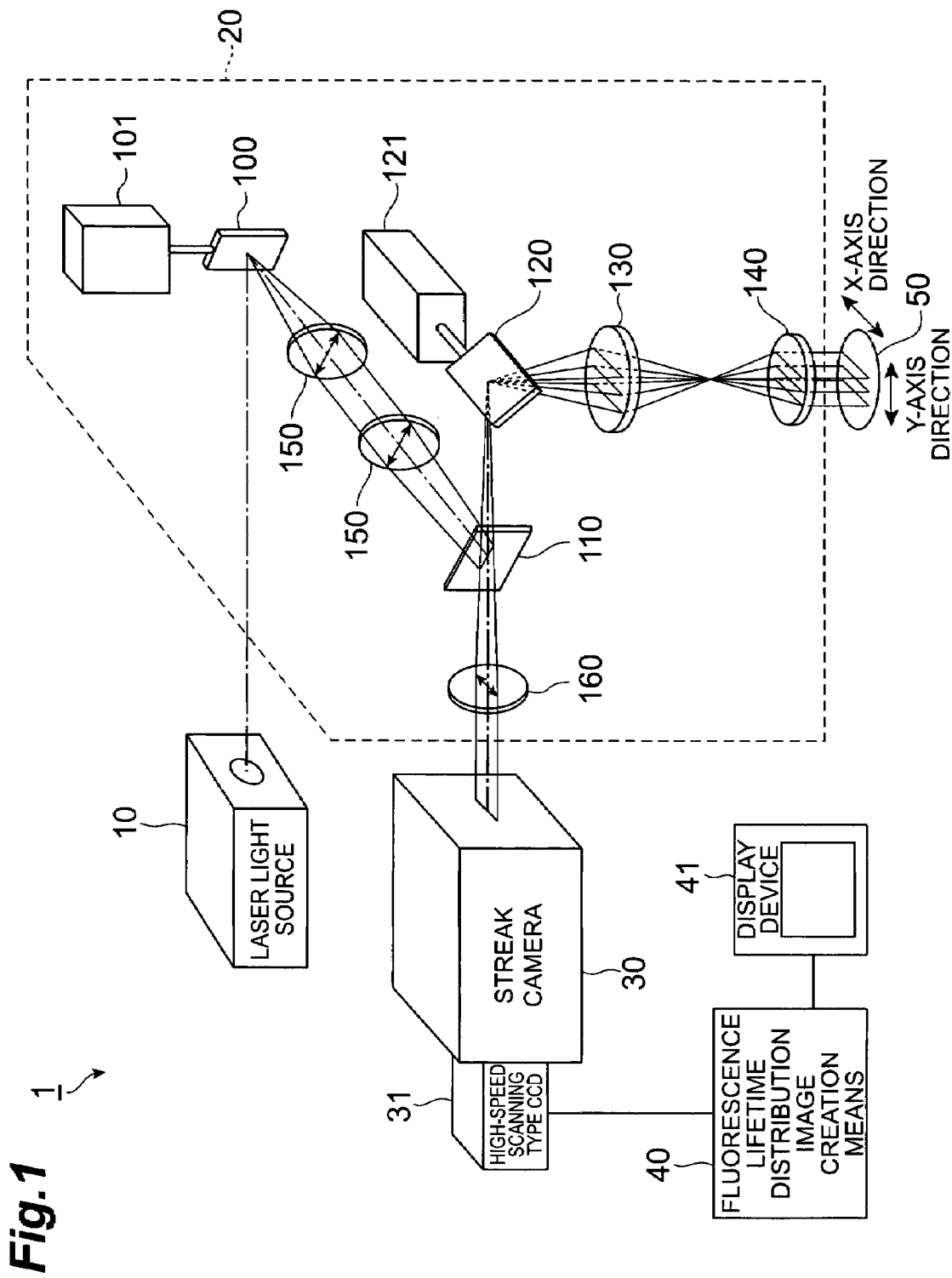
FIG. 1 is an arrangement diagram of a fluorescence lifetime distribution image measurement device of an embodiment.

FIG. 1 is an arrangement diagram showing the general arrangement of a fluorescence lifetime distribution image measurement device of an embodiment.

With this embodiment's fluorescence lifetime distribution image measurement device 1, pulse excitation light is illuminated onto sample 50, which contains fluorescent molecules, and the lifetimes of the fluorescences emitted from this sample 50 are measured. This fluorescence lifetime distribution image measurement device 1 is equipped with a laser light source 10, a measurement optical system 20, a streak camera 30, and a fluorescence lifetime distribution image creation means 40.

Laser light source 10 repeatedly outputs pulse excitation light to be illuminated onto sample 50 and, for example, an ultrashort light pulse (femtosecond pulse) laser light source, such as a titanium sapphire laser, etc., is used favorably.

Measurement optical system 20, which is disposed to the side of laser light source 10, is for guiding and illuminating the pulse excitation light, emitted from laser light source 10, onto sample 50 and guiding and outputting the fluorescences, emitted from sample 50, to the streak camera and has a first scanning means 100, a light separation means 110, a second scanning means 120, an excitation light optical system 130, an objective optical system 140, a pupil relay optical system 150, and an image forming optical system 160.

First scanning means 100, which is disposed to the side of laser light source 10, is driven by a first scanner driver 101 and outputs the pulse excitation light, emitted from laser light source 10, to pupil relay optical system 150 upon scanning the pulse excitation light in a first direction (X-axis direction). For example, a galvanomirror, etc., is used favorably as this scanning means.

Pupil relay optical system 150, which is disposed to the side of first scanning means 100, is positioned so that first scanning means 100 and second scanning means 120 will be in a conjugate relationship and guides the pulse excitation light, arriving from first scanning means 100, to second scanning means 120 via light separation means 110.

Light separation means 110, which is disposed to the side of pupil relay optical system 150, reflects and outputs the pulse excitation light, arriving from pupil relay optical system 150, to second scanning means 120 and transmits and outputs the fluorescences, arriving from second scanning means 120, to image forming optical system 160. For example, a dichroic mirror, etc., is used favorably as this light separation means.

Second scanning means 120, which is disposed to the side of light separation means 110, is driven by a second scanner driver 121 and outputs the pulse excitation light, arriving from light separation means 110, to excitation light optical system 130 upon scanning the pulse excitation light in a second direction (referred to hereinafter as the "Y-axis direction"), which is perpendicular to the first direction (referred to hereinafter as the "X-axis direction") and outputs the fluorescences, arriving from excitation light optical system 130, to the light separation means 110 upon scanning the fluorescences in the Y-axis direction, perpendicular to the X-axis direction. For example, a galvanomirror, etc., is used favorably as this scanning means.

Excitation light optical system 130, which is positioned below second scanning means 120, is positioned so that second scanning means 120 and objective optical system 140 will be in a conjugate relationship, outputs the pulse excitation light, arriving from second scanning means 120, to objective optical system 140, and outputs the fluorescences, arriving from objective optical system 140, to second scanning means 120.

Objective optical system 140, which is positioned below excitation light optical system 130, converges and illuminates the pulse excitation light, arriving from excitation light optical system 130, onto sample 50, and outputs the fluorescences, which are emitted from sample 50 when the pulse excitation light is illuminated onto sample 50, to excitation light optical system 130.

Image forming optical system 160, which is disposed to the side of light separation means 110, is positioned so that sample 50 and the photoelectric surface of streak camera 30 will be in a conjugate relationship, and forms an image of the fluorescences, arriving from light separation means 110, on the photoelectric surface of streak camera 30.

Streak camera 30, which is disposed to the side of image forming optical system 160, is for recording the variations with time of the fluorescence intensities of the fluorescences output from measurement optical system 20, and high-speed scanning type CCD 31 picks up the optical image on the fluorescent screen of streak camera 30.

Fluorescence lifetime distribution image preparation means 40 calculates the fluorescence lifetimes based on the variations with time of the fluorescence intensities that have been recorded by streak camera 30 and prepares a fluorescence lifetime distribution image.

The actions of this embodiment's fluorescence lifetime distribution image measurement device 1 shall now be described along with the fluorescence lifetime distribution image measurement method.

With this embodiment's fluorescence lifetime distribution image measurement device 1, the pulse excitation light emitted from laser light source 10 is output to measurement optical system 20, the pulse excitation light, output to measurement optical system 20, is scanned and output in the X-axis direction by first scanning means 100, the pulse excitation light, scanned and output in the X-axis direction, is output by pupil relay optical system 150 to light separation means 110, the pulse excitation light, output to light separation means 110, is scanned and output in the Y-axis direction perpendicular to the X-axis direction by second scanning means 120, and the pulse excitation light, scanned and output in the Y-axis direction, is converged and illuminated onto sample 50 by objective optical system 140. The fluorescences, emitted from sample 50 when the pulse excitation light is illuminated onto sample 50, are output by objective optical system 140 to excitation light optical system 130, the fluorescences, output to excitation light optical system 130, are output by excitation light optical system 130 to second scanning means 120, the fluorescences, output to second scanning means 120, are scanned in the Y-axis direction perpendicular to the X-axis direction and output to light separation means 110 by second scanning means 120, the fluorescences, output to light separation means 110, are output by light separation means 110 to image forming optical system 160, the fluorescences, output to image forming optical system 160, are output by image forming optical system 160 to streak camera 30, and the fluorescences, output to streak camera 30, are recorded as the variations with time of the fluorescence intensities of the fluorescences by streak camera 30. Then based on the variations with time of the fluorescence intensities recorded by streak camera 30, the fluorescence lifetimes are calculated and the fluorescence lifetime distribution image is prepared.

With this embodiment's fluorescence lifetime distribution image measurement method, pulse excitation light, which is emitted in a first step and has a pulse width of no more than 150 fs, a peak power density at the convergence point of no less than $1 \times 10^5 W/cm^2$, and wavelength of no less than $\lambda$ and no more than $2\lambda$, with $\lambda$ being the maximum wavelength of light that can excite the sample 50 and cause fluorescence, is scanned in the X-axis direction in a second step. The pulse excitation light, which has been scanned in the X-axis direction, is scanned in the Y-axis direction, perpendicular to the X-axis direction, in a third step. The pulse excitation light, which has been scanned in the X-axis direction and the Y-axis direction, respectively, is converged in the interior of the sample in a fourth step, and the variations with time of the fluorescence intensities of the fluorescences emitted due to illumination of the converged pulse excitation light are recorded in a fifth step. In a sixth step, the fluorescence lifetimes are calculated based on the recorded variations with time of the fluorescence intensities and a fluorescence lifetime distribution image is prepared.

Figure 2:
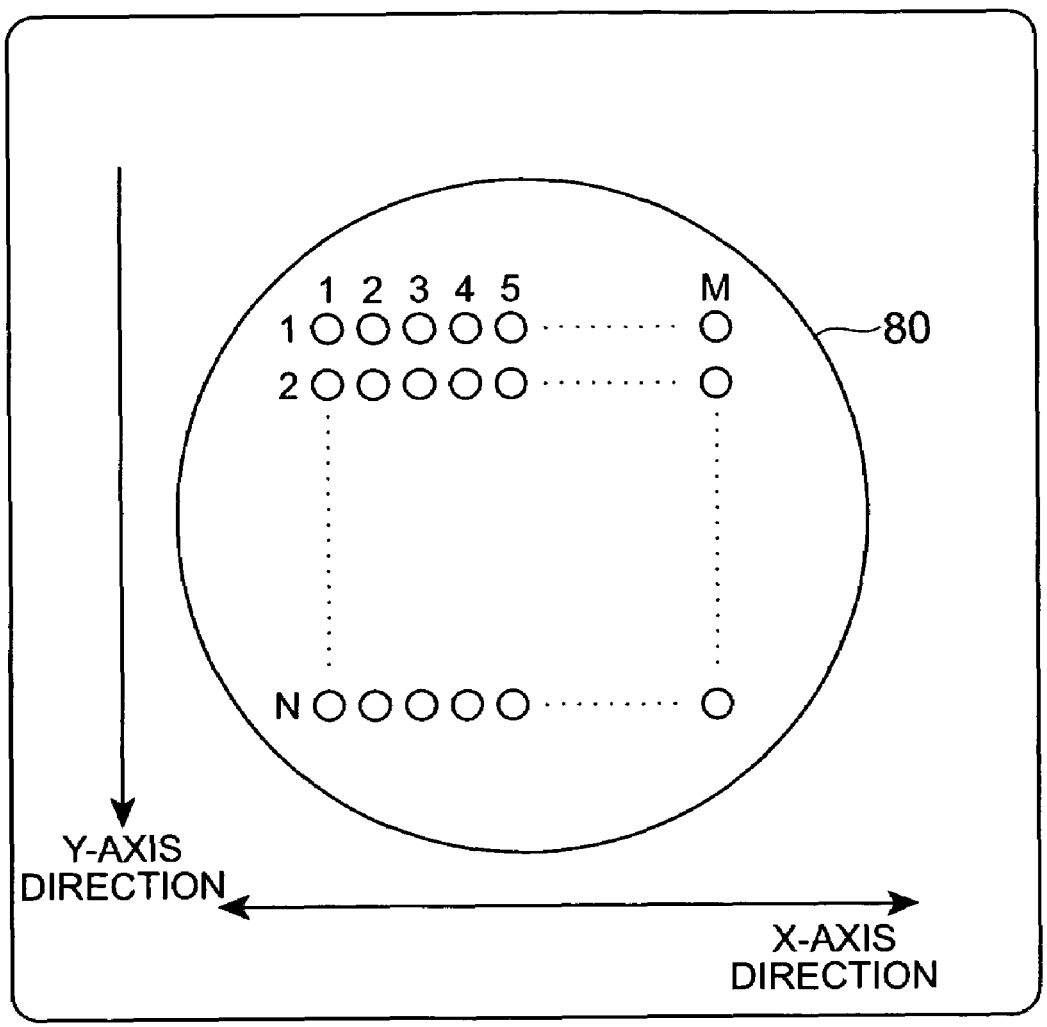
FIG. 2 is a diagram showing the scanning states of a sample under a microscope in the embodiment.

FIG. 2 shows the scanning states of a cell or other sample 50 under microscope objective optical system 140. This FIGURE schematically shows how a spot-like pulse excitation light is scanned at high speed in the X-axis direction (1, 2, 3, . . . , M) of sample 50 and being scanned furthermore in the Y-axis direction (1, 2, 3, . . . , N) as well. The scan distance in the X-axis direction corresponds to the slit length of the photoelectric surface of streak camera 30. The scanning period in the X-axis direction is set to 100 Hz to 1 kHz.

Since the frequency of the pulse excitation light is approximately 1 MHz to 80 MHz and X-axis scanning means 20 scans at a rate of 100 Hz to 1 kHz, light spots of a diameter of approximately 0.5 μm, resulting from the convergence of pulse excitation light, become aligned in a pseudo-slit-like manner by the scanning in the X-axis direction.

Here, in regard to the scanning in the Y-axis direction, second scanning means 120 (galvanomirror) is positioned to the rear of light separation means 110 (dichroic mirror) and second scanning means 120 (galvanomirror) is positioned at the rear focal plane of excitation light optical system 130 (pupil projection lens) and scans the pulse excitation light only in the Y-axis direction. The fluorescences that are emitted from the sample is de-scanned by passage through the second scanning means and is then directed to streak camera 30. The image that is scanned along the Y-axis direction of excitation light optical system 130 (pupil projection lens) thus takes the form of being scanned only in the X-axis direction and is always imaged onto the photoelectric surface of streak camera 30.

By image forming optical system 160, the fluorescences are imaged as a slit image on the photoelectric surface of a streak tube via the slit of streak camera 30. When a fluorescence enters the slit and reaches the photoelectric surface, this fluorescence is converted in electrons of a number corresponding to the light intensity by the photoelectric surface and these electrons are accelerated by an accelerating electrode and thereby emitted toward the fluorescent surface. When these electrodes pass between sweeping electrodes, high-speed sweeping is carried out by the high voltage that is applied in matched timing to the sweeping electrodes. The set of electrons that are thereby lagged little by little with respect to each other are deflected at angles in the vertical direction that differ little by little and then enter an MCP (microchannel plate). In the process of passing through the MCP the set of electrons are multiplied in number by several tens of thousands of times and thereafter converted into light by colliding with the fluorescent screen. On the fluorescent screen, fluorescence images are aligned successively downwards with the fluorescence image corresponding to the light pulse that became incident the earliest being positioned at the uppermost position. The vertical direction on the fluorescent screen thus becomes the time axis. Also, the brightness of each fluorescence image is proportional to the intensity of the corresponding fluorescence. The horizontal direction position of a fluorescence image corresponds to the horizontal position of the fluorescence. The amplified streak image on the fluorescent screen is captured by high-speed scanning type CCD 31. Here, high-speed scanning type CCD 31 begins exposure in accordance with a command signal from a CCD camera drive circuit that has received a CCD trigger signal from the streak sweep circuit.

FIGS. 6A to F are diagrams illustrating the operation timing of this embodiment's fluorescence lifetime distribution image measurement device 1. Here, the period of the pulse excitation light emitted by laser light source 10 is synchronized with the sweep period of streak camera 30. A streak image is thus acquired according to the fluorescences emitted from sample 50 as a result of illumination of the pulse excitation light and this streak image is captured by high-speed scanning type CCD 31.

Also as shown in FIGS. A to F, the exposure time of high-speed scanning type CCD 31 and the Y-axis sweep timing are synchronized. The exposure time of high-speed scanning type CCD 31 is approximately 200 ms, and during this interval, second scanning means 120 is stopped. When approximately 200 ms elapses and the image pickup of one CCD image is ended, second scanning means 120 (galvanomirror) is moved and the image pickup of the next image is performed.

By repeating this N times, two-dimensional scanning of sample 50 is performed as shown in FIG. 2.

Figure 3:
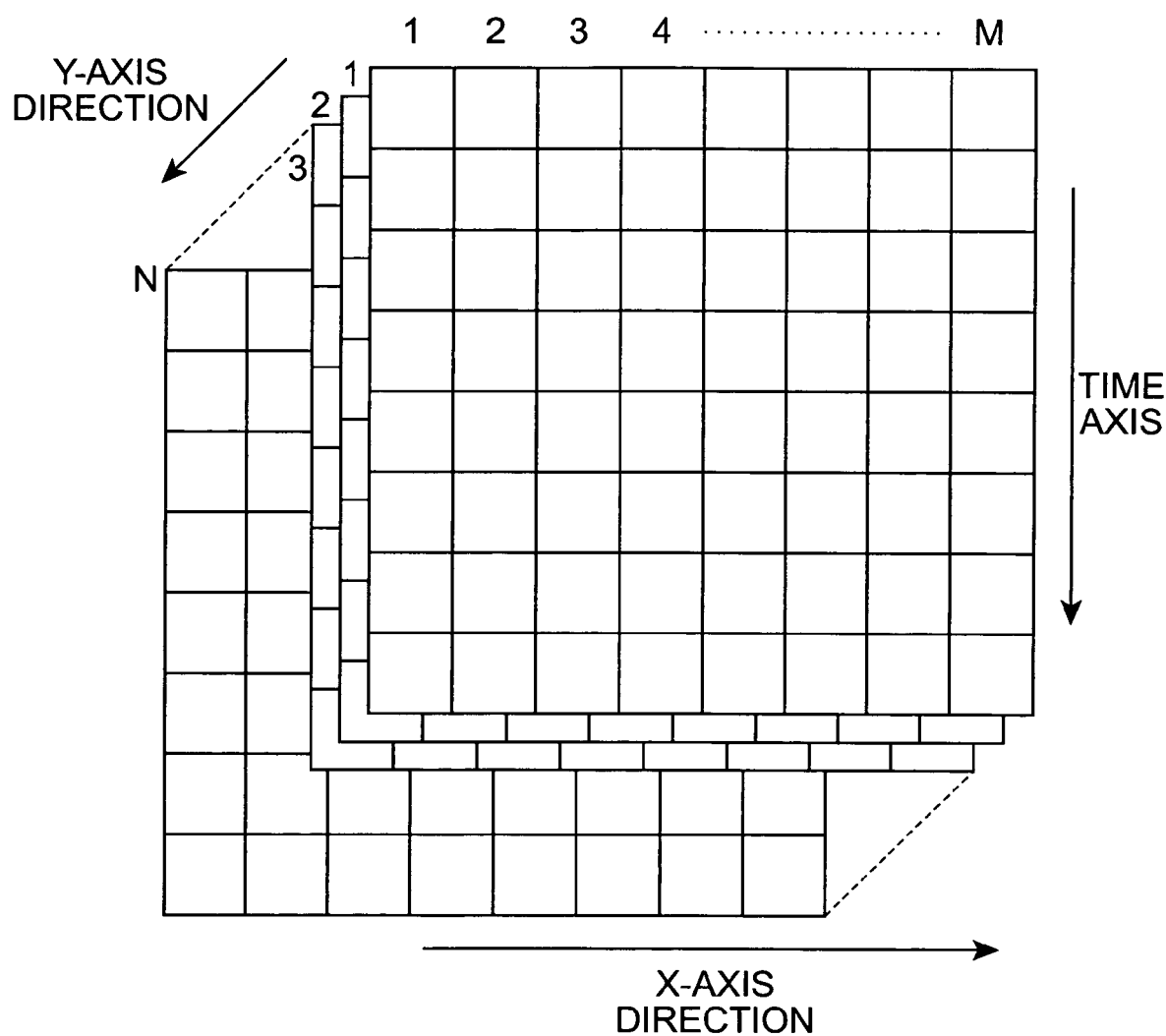
FIG. 3 is a diagram showing images, of fluorescence streak images recorded by a streak camera of the embodiment, which are captured by a high-speed scanning type CCD.
Figure 4:
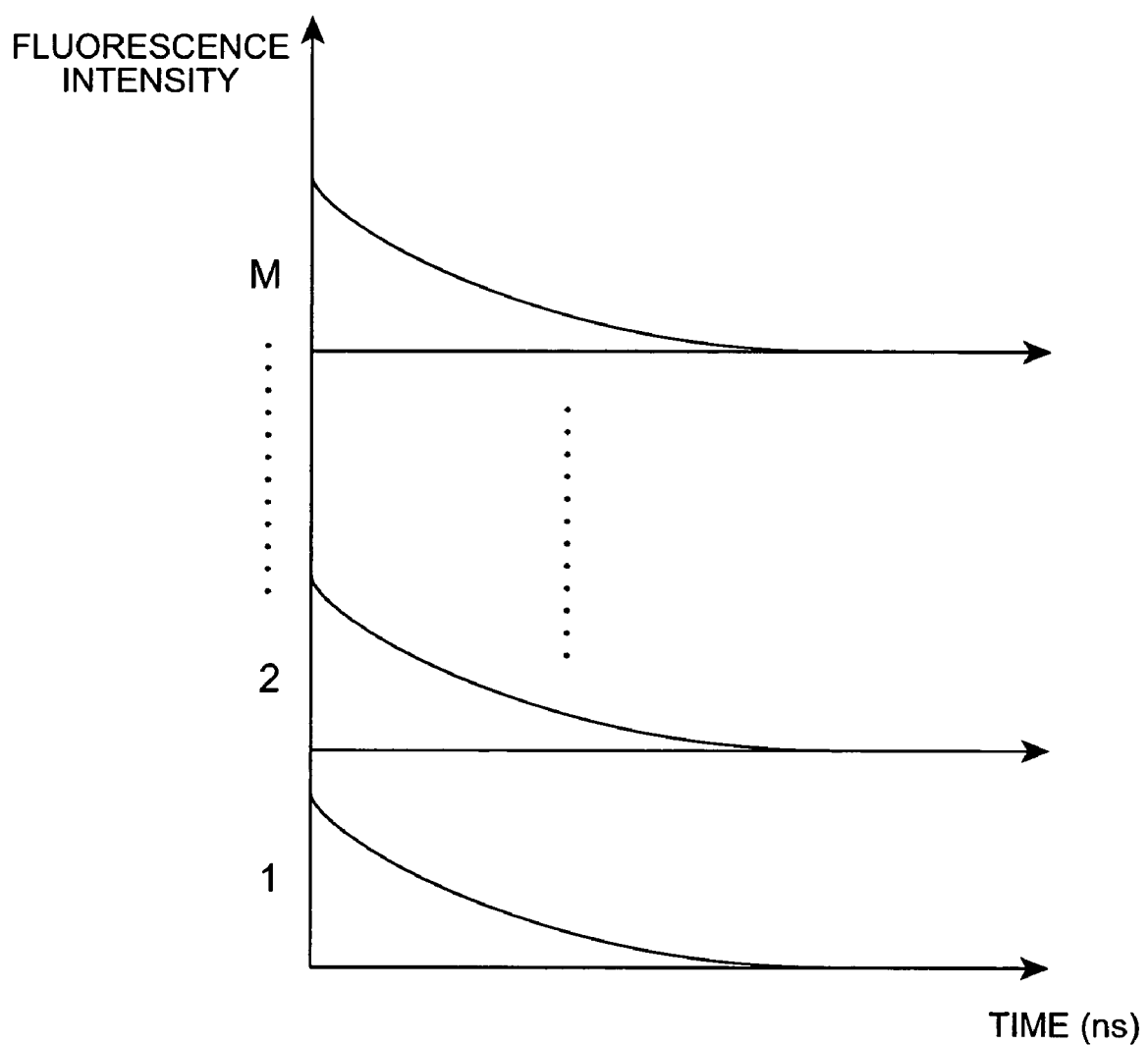
FIG. 4 is a diagram illustrating the variations with time of the fluorescence intensities at respective scanning points.

FIG. 3 is a diagram showing images, of fluorescence streak images recorded by streak camera 30 of the present embodiment, which have been captured by high-speed scanning type CCD 31. Each image is acquired by fixing second scanning means 120 during the exposure time of high-speed scanning type CCD 31 and exposing high-speed scanning type CCD 31 during this interval. Streak images, each corresponding to the intensity of fluorescence emitted upon excitation by the pulse excitation light that has been scanned in the X-axis direction (1, 2, 3, . . . , M), are acquired. Here, the horizontal direction of the image corresponds to the X-axis direction and the vertical direction of the image is the time axis. Thus as shown in FIG. 4, for each of the vertical lines, respectively corresponding to scanning points 1 to M, the time variation data of the fluorescence intensity at each scanning point can be obtained. Here, if Y-axis scanning is performed N times, N images are acquired.

FIG. 5 is a diagram showing a fluorescence lifetime profile of the present embodiment. The time it takes for the fluorescence intensity to decay to 1/e of the peak value is deemed to be the fluorescence lifetime value. With fluorescence lifetime distribution image creation means 40, based on the fluorescence intensity time variation data that have been acquired by high-speed scanning type CCD 31, the fluorescent lifetime values of sample 50 corresponding to the respective convergence points of 1 to M are calculated from each vertical line.

To calculate the fluorescence lifetime, the fluorescence intensity time variation data, which have been obtained for each vertical line of the CCD, are subject to a fitting calculation of fitting a predetermined curve (function system), etc., to the time variation, and the fluorescence lifetime of each fluorescence is thereby calculated. By carrying out this process for M lines in a single image and then furthermore carrying out the same process on each of the N images, the fluorescence lifetime value data of the respective scanning points are obtained.

By displaying the fluorescence lifetime values of the respective scanning points that are thus obtained by displaying different colors in accordance with the magnitude of the lifetime values at the respective scanning points, a fluorescence lifetime distribution image (FLIM image) of a cell or other sample 50 can be obtained.

Fluorescence lifetime distribution image preparation means 40 is preferably connected to a display device 41 (see FIG. 1) for displaying as necessary the fluorescence lifetime distribution image obtained by fluorescence lifetime distribution preparation means 40.

This embodiment's objective optical system 140 is preferably positioned at a position at which the convergence point is set inside sample 50, and the pulse excitation light preferably has a pulse width of no more than 150 fs, a peak power density at the convergence point of no less than $1\times10^5$ W/cm$^2$, and a wavelength of no less than λ and no more than 2λ, where λ is the maximum wavelength of light that can excite sample 50 and cause fluorescence. In this case, two-photon excitation can be caused by the pulse excitation light at the convergence point.

Also, the wavelength of the pulse excitation light is preferably no less than 750 nm and no more than 1000 nm. Two-photon excitation can thereby be caused in a cell or other sample stained by a fluorescent protein or a fluorescent dye.

With the present embodiment, a titanium sapphire laser, of a pulse width of no more than 150 fs and a frequency of 76 MHz, was used as laser light source 10. Also, a 40-times magnification oil-immersion or water-immersion objective lens was used in objective optical system 140. In this case, the laser output is approximately 8 mW. In the case where laser light source 10 of a frequency of 1 MHz is used, the laser output will be 0.1 mW.

With this embodiment, the position of objective optical system 140 preferably moves along a direction perpendicular to both the X-axis direction and the Y-axis direction. Since this enables measurement of the fluorescence lifetime in the depth direction of sample 50 as well, a three-dimensional fluorescence lifetime distribution image can be obtained.

With a long wavelength laser, since the laser reaches deeper parts inside a tissue than with a short wavelength laser, comparatively deep regions of a sample can be observed.

Also, though with single-photon excitation, since excitation occurs in the vicinity of the convergence point as well, spatial resolution in the depth direction cannot be attained, with two-photon excitation, since excitation occurs only at the convergence point of the pulse excitation light of a diameter of approximately 0.5 μm, excellent spatial resolution can be attained. Thus by moving objective optical system 140 and thereby moving the convergence point in the depth direction of sample 80, mapping in the depth direction can be performed. A three-dimensional fluorescence lifetime distribution image can thus be obtained.

As has been described above, by this invention, a fluorescence lifetime distribution image measurement device and measurement method, with which damaging of a cell or other sample can be minimized and measurement within a short time can be realized, can be provided.

INDUSTRIAL APPLICABILITY

This invention is used, for example, for the analysis of gene expression, protein interactions, etc., inside a cell.

The invention claimed is:

1. A fluorescence lifetime distribution image measurement device for measuring the distribution in a sample of the lifetimes of fluorescences emitted from said sample upon illumination of said sample with pulse excitation light, said fluorescence lifetime distribution image measurement device comprising:

a laser light source for emitting said pulse excitation light;

a measurement optical system for guiding said pulse excitation light emitted by said laser light source to said sample and thereby illuminating said sample, and guiding and outputting said fluorescences emitted from said sample;

a streak camera for recording the variations with time of the fluorescence intensities of said fluorescences that arrive upon being output from said measurement optical system; and fluorescence lifetime distribution image creation means for calculating the fluorescence lifetimes based on said variations with time of the fluorescence intensities recorded by said streak camera and creating a fluorescence lifetime distribution image;

said measurement optical system comprising first scanning means, light separation means, second scanning means, and an objective optical system, said first scanning means scanning said pulse excitation light, emitted by said laser light source, in a first direction, said light separation means guiding said pulse excitation light, arriving from said first scanning means, to said second scanning means and guiding said fluorescences, arriving from the second scanning means, to said streak camera, said second scanning means scanning said pulse excitation light, arriving from said light separation means, in a second direction perpendicular to said first direction and guiding said fluorescences, output and arriving from said objective optical system, to said light separation means so that said fluorescences pass through the same optical path that said pulse excitation light passed through in being directed from said light separation means to said second scanning means, and said objective optical system converging and illuminating said pulse excitation light that has been scanned in said first direction and second direction respectively onto respective scanning points in said sample and outputting the fluorescences, which are emitted from said respective scanning points upon illumination of said pulse excitation light, to said second scanning means.

2. The fluorescence lifetime distribution image measurement device according to claim 1, wherein said objective optical system is positioned at a position at which the convergence points are set inside the sample; and said pulse excitation light has a pulse width of no more than 150 fs, a peak power density at said convergence point of no less than $1 \times 10^5$ W/cm$^2$, and a wavelength of no less than $\lambda$ and no more than $2\lambda$, where $\lambda$ is the maximum wavelength of light that can excite said sample and cause fluorescence.

3. The fluorescence lifetime distribution image measurement device according to claim 2, wherein said pulse excitation light has a wavelength of no less than 750 nm and no more than 1000 nm.

4. The fluorescence lifetime distribution image measurement device according to claim 2, wherein the position of said objective optical system moves along a direction perpendicular to both the first direction and the second direction.

5. The fluorescence lifetime distribution image measurement device according to claim 1, wherein said first scanning means and second scanning means are respectively galvanomirrors, and said light separation means is a dichroic mirror.

6. A fluorescence lifetime distribution image measurement method for measuring the distribution in a sample of the lifetimes of fluorescences emitted from said sample upon illumination of said sample with pulse excitation light, said fluorescence lifetime distribution image measurement method comprising:

a first step of generating said pulse excitation light of a pulse width of no more than 150 fs, a peak power density at the convergence point of no less than $1 \times 10^5$ W/cm$^2$, and a wavelength of no less than $\lambda$ and no more than $2\lambda$, where $\lambda$ is the maximum wavelength of light that can excite the sample and cause fluorescence;

a second step of scanning said pulse excitation light in a first direction;

a third step of scanning said pulse excitation light, which has been scanned in said first direction, in a second direction perpendicular to said first direction;

a fourth step of converging and illuminating said pulse excitation light, which has been scanned in said first direction and second direction, respectively, onto respective scanning points inside said sample;

a fifth step of recording the variations with time of the fluorescence intensities of said fluorescences that are emitted from said respective scanning points by the illumination of said converged pulse excitation light; and a sixth step of calculating the fluorescence lifetimes based on said recorded variations with time of the fluorescence intensities, and creating a fluorescence lifetime distribution image, wherein at least the fifth step is performed using a streak camera.

7. A fluorescence lifetime distribution image measurement device according to claim 1, wherein the streak camera has a photoelectric surface with a slit having a predetermined slit length and a scan distance of the pulse excitation light corresponds to the predetermined slit length.

8. A fluorescence lifetime distribution image measurement device according to claim 1, wherein the streak camera comprises a CCD and the fluorescence light time distribution image creation means makes a fluorescence lifetime profile based on a streak image outputted from the CCD.

* * * * *